(12) United States Patent
Hu et al.

(10) Patent No.: US 8,279,437 B2
(45) Date of Patent: Oct. 2, 2012

(54) MULTI-WAVELENGTH RAMAN LIGHT DETECTION FOR DETECTING A SPECIES

(75) Inventors: Min Hu, Sunnyvale, CA (US); Alexandre M. Bratkovski, Mountain View, CA (US); Huel Pei Kuo, Cupertino, CA (US); Jingjing Li, Palo Alto, CA (US); Zhiyong Li, Redwood City, CA (US); Fung Suong Ou, Palo Alto, CA (US); Michael Josef Stuke, Palo Alto, CA (US); Michael Renne Ty Tan, Menlo Park, CA (US); Shih-Yuan Wang, Palo Alto, CA (US); Wei Wu, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 267 days.

(21) Appl. No.: 12/836,097

(22) Filed: Jul. 14, 2010

(65) Prior Publication Data

US 2012/0013902 A1 Jan. 19, 2012

(51) Int. Cl.
*G01J 3/44* (2006.01)

(52) U.S. Cl. ........................................................ 356/301

(58) Field of Classification Search .................... None
See application file for complete search history.

(56) References Cited

U.S. PATENT DOCUMENTS

| | | | |
|---|---|---|---|
| 7,267,948 B2 | 9/2007 | Vo-Dinh | |
| 7,342,656 B2 | 3/2008 | Islam et al. | |
| 7,511,285 B2 | 3/2009 | Bernstein | |
| 7,659,977 B2 | 2/2010 | Koo | |
| 7,969,578 B2 * | 6/2011 | Yun et al. | 356/497 |
| 2005/0110990 A1 | 5/2005 | Koo et al. | |
| 2009/0323061 A1 * | 12/2009 | Novotny et al. | 356/336 |
| 2010/0092942 A1 | 4/2010 | Siegel et al. | |

* cited by examiner

*Primary Examiner* — Tu Nguyen (57) ABSTRACT

An apparatus for detecting at least one species using Raman light detection includes at least one laser source for illuminating a sample containing the at least one species. The apparatus also includes a modulating element for modulating a spatial relationship between the sample and the light beams to cause relative positions of the sample and the light beams to be oscillated, in which Raman light at differing intensity levels are configured to be emitted from the at least one species based upon the different wavelengths of the light beams illuminating the sample. The apparatus also includes a Raman light detector and a post-signal processing unit configured to detect the at least one species.

20 Claims, 7 Drawing Sheets

MULTI-WAVELENGTH RAMAN LIGHT
DETECTION FOR DETECTING A SPECIES

STATEMENT OF GOVERNMENT INTEREST

This invention was made with government support under Contract No. HR0011-09-3-0002, awarded by Defense Advanced Research Projects Agency. The government has certain rights in the invention.

BACKGROUND

Raman spectroscopy has been utilized for a number of years to identify single molecules from various types of samples. Raman spectroscopy, more particularly, has been utilized to identify the vibrational modes of molecules to distinguish between different molecular species. The probability, however, of a Raman interaction occurring between an excitatory beam of light and an individual molecule in a sample is very low, for instance, $10^{-30}$ cm$^2$ for CN. As such, the use of Raman spectroscopy to identify individual molecules has been relatively limited.

One approach to enhancing the Raman spectroscopy effect is to place the molecules near roughened silver surfaces. The surface enhanced Raman spectroscopy (SERS) effect is related to the phenomenon of plasmon resonance, in which metal nanoparticles exhibit an increased optical resonance in response to incident electromagnetic radiation, due to the collective coupling of conduction electrons in the metal. Attempts at implementing SERS have included coating metal nanoparticles or fabricating rough metal films on the surface of the substrate and then applying a sample to the metal-coated surface.

BRIEF DESCRIPTION OF THE DRAWINGS

Embodiments are illustrated by way of example and not limited in the following figure(s), in which like numerals indicate like elements, in which.

DETAILED DESCRIPTION

For simplicity and illustrative purposes, the principles of the embodiments are described by referring mainly to examples thereof. In the following description, numerous specific details are set forth in order to provide a thorough understanding of the embodiments. It will be apparent however, to one of ordinary skill in the art, that the embodiments may be practiced without limitation to these specific details. In other instances, well known methods and structures are not described in detail so as not to unnecessarily obscure the description of the embodiments.

Disclosed herein is an apparatus for detecting at least one species in a sample using multi-wavelength Raman light detection, which results in a relatively high level of precision. The accuracy of the species detection is relatively high because the apparatus disclosed herein significantly increases the signal-to-noise ratio in the processing of the Raman light emissions from the species. As discussed in greater detail herein below, a spatial relationship between light beams having different wavelengths and the sample is modulated at an identified frequency to cause the sample to be irradiated by light beams having different wavelengths. In addition, a post-signal processing unit is configured to process the detected Raman light emitted from the species at the identified frequency. In one regard, the post-signal processing unit or a computing device is configured to lock into the identified frequency and to filter out signals in other frequencies when processing the detected Raman light, which results in the increased signal-to-noise ratio.

Figure 1:
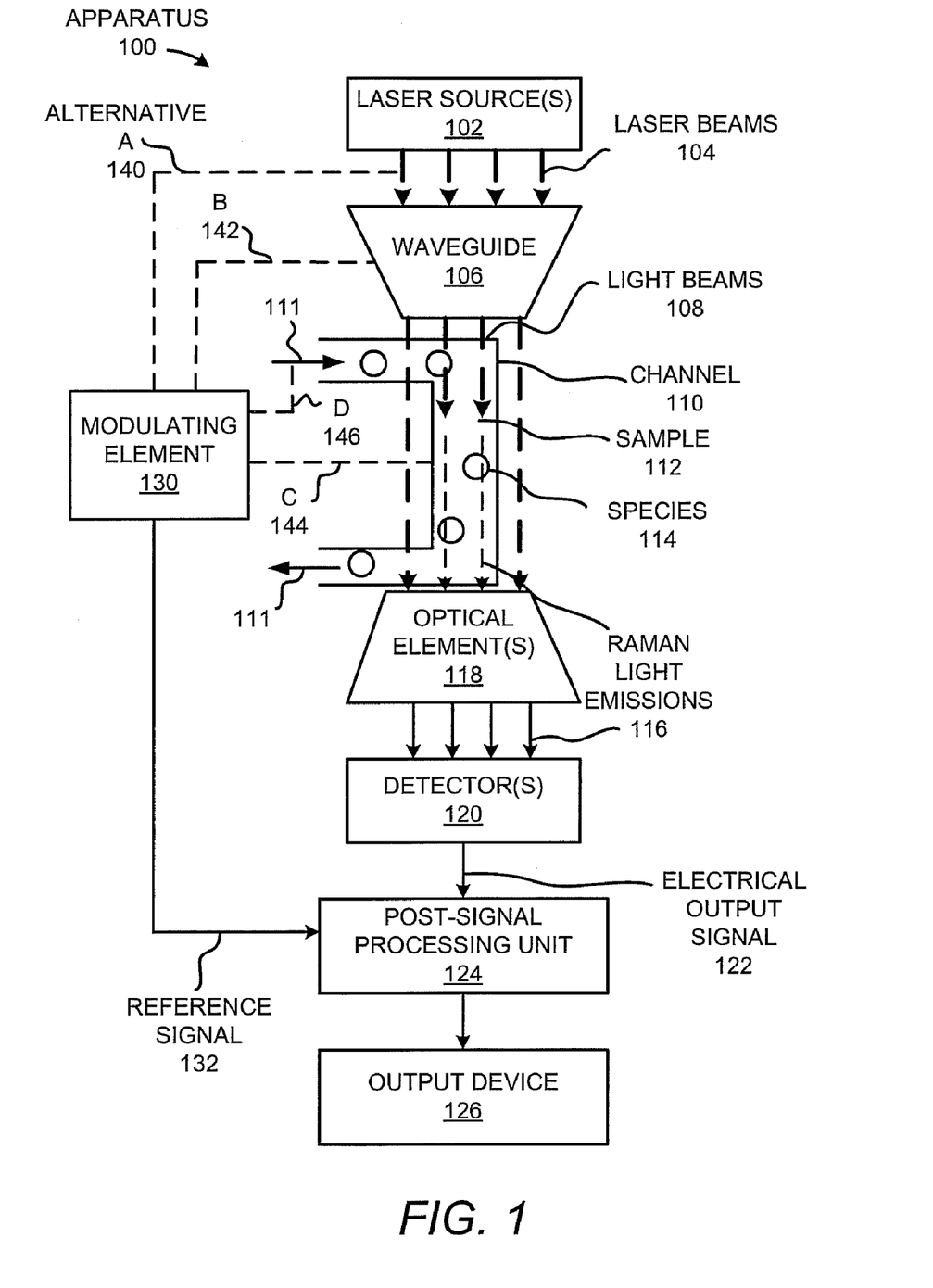
FIG. 1 a simplified schematic diagram of an apparatus for detecting at least one species in a sample using Raman light detection, according to an embodiment of the invention.

With reference first to FIG. 1, there is shown a simplified schematic diagram of an apparatus 100 for detecting at least one species in a sample using multi-wavelength Raman light detection, according to an embodiment. It should be understood that the apparatus 100 depicted in FIG. 1 may include additional components and that some of the components described herein may be removed and/or modified without departing from a scope of the apparatus 100. It should also be understood that the components depicted in FIG. 1 are not drawn to scale and thus, the components may have different relative sizes with respect to each other than as shown therein.

As shown, the apparatus 100 includes at least one laser source 102 configured to emit one or more laser beams 104. In one example, the apparatus 100 includes a single laser source 102 configured to emit a single laser beam 104. In this example, the single laser source 102 includes an optical element (not shown), such as a prism, or other optical element, configured to split the laser beam 104 into a plurality of light beams 108. In another example, the apparatus 100 includes a plurality of laser sources 102, in which each of the plurality of laser sources 102 is configured to emit one of a plurality of light beams 108 at different wavelengths. The plurality of different wavelengths may range between, for instance, wavelengths of around 400-600 nm. In any of the examples discussed above, a plurality of light beams 108 having different wavelengths with respect to each other illuminate a sample 112, for instance, contained in a channel 110, as discussed in greater detail herein below. The sample 112 may, however, be contained on a substrate or other container without departing from a scope of the invention.

The light beams 108 are depicted as being transmitted through a waveguide 106, such as an optical fiber, prior to irradiating the sample 112. Although not explicitly shown, the light beams 108 may traverse an optical path containing one or more optical devices configured to manipulate, for instance, the placements, directions, intensities, etc., of the light beams 108. These optical devices may include, for instance, an electro-optic deflector, prism, mirrors, etc.

In one embodiment, the sample 112 generally comprises a fluid material configured to flow through the channel 110 as indicted by the arrows 111. The sample 112 may be contained in a reservoir (not shown) and forced through the channel 110 through operation of a pump 230 (FIG. 2B). In addition, the channel 110 may comprise a nanometer to micrometer width.

As further shown in FIG. 1, the light beams 108 are configured to illuminate one or more species 114 contained in the sample 112 and to cause a Raman effect on the species 114 and thereby cause Raman light to be emitted or scattered from the species 114. The species 114 may comprise a molecule, a biological particle, a cell, etc. The Raman light emitted 116 from the species 114 is collected by one or more optical elements 118, which may include, for instance, a condenser lens system, a spectrometer, a filter, etc. For instance, the emitted Raman light 116 is focused by the condenser lens system and undergoes wavelength dispersion in the spectrometer prior to reaching one or more optical detectors 120 to, for instance, convert the emitted Raman light 116 to a monochromated light. The optical detector(s) 120 receives the emitted Raman light 116 and converts it to an electrical output signal 122, which is transmitted to a post-signal processing unit 124. Although not shown, the electrical output signal 122 may be amplified prior to or during transmission to the post-signal processing unit 124.

The components of the apparatus 100 may be arranged in any suitable manner. For instance, the optical elements 118 and the detector(s) 120 may be arranged on the same side of the species 114 as the laser beams 104. In another example, the channel 110 may be supported on a transparent substrate (not shown), such as glass, and the optical elements 118 and the detector(s) 120 may be arranged to capture Raman light 116 that is emitted through the channel 110.

Also depicted in FIG. 1 is a modulating element 130 for modulating a spatial relationship between the sample 112 and the light beams 108 to cause relative positions of the sample 112 and the light beams 108 to be oscillated. The modulating element 130 is configured to modulate the spatial relationship in any of a plurality of different manners as discussed in greater detail below with respect to alternatives 140-146. By way of example, the modulating element 130 is configured to cause the channel 110 to oscillate across the light beams 108, which have different wavelengths with respect to each other, such that, the sample 112 is sequentially illuminated by the different light beams 108. As another example, the modulating element 130 is configured to cause the light beams 108 to oscillate across the channel 110 to sequentially illuminate the sample 122 with the different light beams 108. These examples are discussed in greater detail herein below with respect to FIG. 2A. As a further example, the modulating element 130 is configured to cause the sample 112 to oscillate within the channel 110 to thereby cause portions of the sample 112 to be sequentially illuminated by the different light beams 108. This example is discussed in greater detail herein below with respect to FIG. 2B.

In any of the examples above, the modulating element 130 may be configured to modulate the spatial relationship between the sample 112 and the light beams 108 at an identified frequency to cause the Raman light 116 to be emitted from the species 114 at the identified frequency. In one example, the amplitude of the modulation is selected to enable the sample 112 to be irradiated by each of the light beams 108 during each modulation cycle or oscillation cycle. Each modulation cycle may comprise a complete displacement of the sample 112 across each of the light beams 108.

In one regard, the post-signal processing unit 124 is configured to implement a lock-in detection technique on the Raman light emission(s) 116 detected by the optical elements(s) 118 while the species 114 is irradiated by each of the different light beams 108. As such, for instance, the post-signal processing unit 124 includes a lock-in amplifier, a boxcar amplifier, a combination of a lock-in amplifier and a boxcar amplifier, or the like, which serves to detect and amplify only the signal component of the electrical output signal 122 from the detector(s) 120 that has the same frequency as that of the identified frequency at which the modulating element 130 modulates either or both of the sample 112 and the light beams 108. More particularly, for instance, the post-signal processing unit 124 may implement a high speed or a programmable monochromater or a multi-wavelength filter to differentiate the Raman signal at each wavelength and thus, the post-signal processing unit 124 may employ a similar processing techniques as those employed in processing single-wavelength detection. Because the post-signal processing unit 124 detects and amplifies only the signal component of the electrical output signal 122 that has the same frequency as that of the identified frequency of a reference signal 132 received from the modulating element 130, the input signal component having a frequency different from that of the reference signal 132 is not sampled. Further, by selecting appropriately the locked-in phase, the post-signal processing unit 124 may sample the signal component ascribable to a particular species 114.

In another regard, the post-signal processing unit 124 is configured to output data pertaining to the results of the post-signal processing on the detected Raman light emissions 116. As shown in FIG. 1, the post-signal processing unit 124 is configured to output the data through an output device 126, which may comprise, for instance, a display, a printer, a computing device, etc., through which the results, such as, whether a species 114 has been detected may be outputted.

Figure 2A:
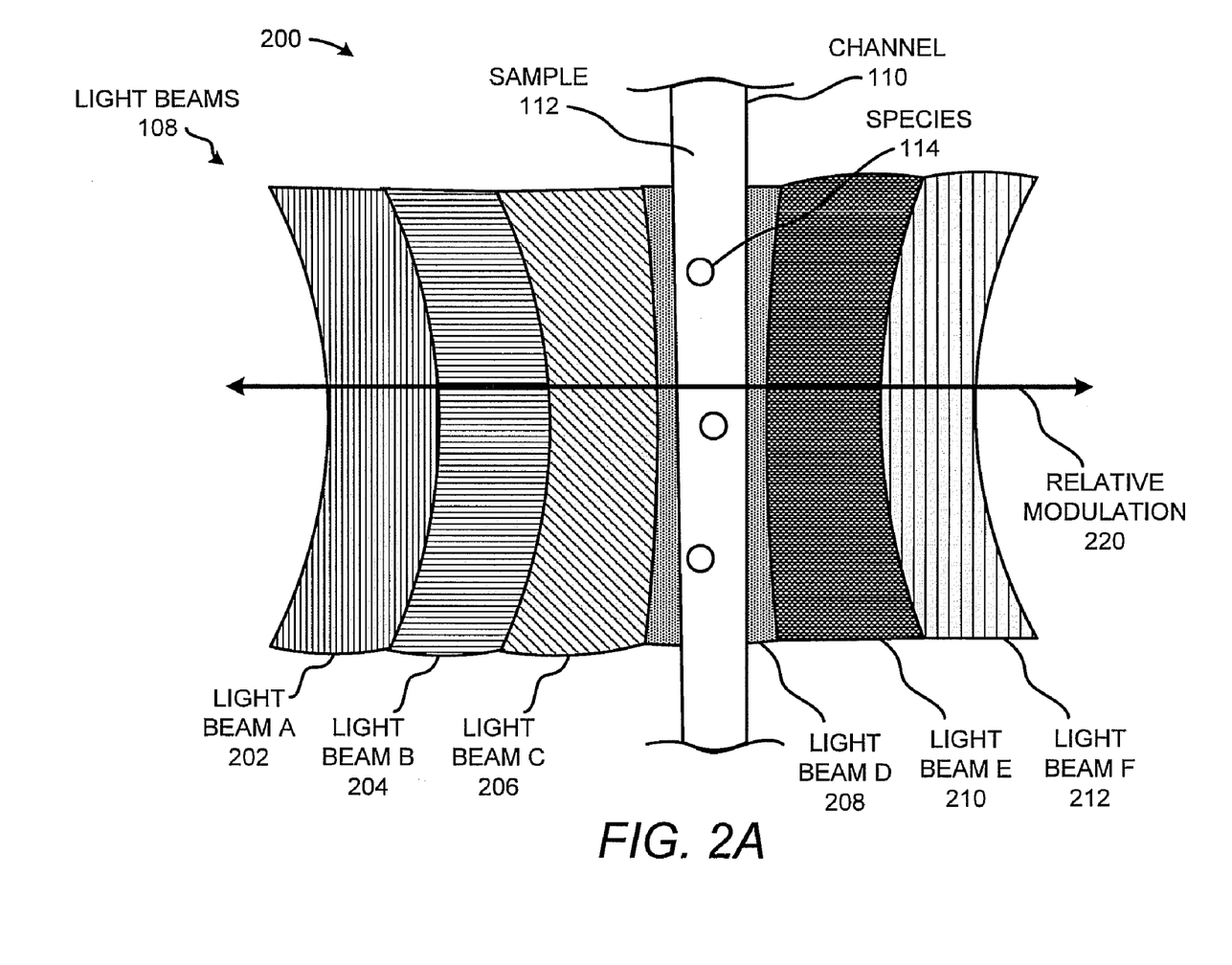
FIGS. 2A and 2B, respectively, illustrate simplified and enlarged schematic diagrams of the sample depicted in FIG. 1, according to embodiments of the invention.
Figure 2B:
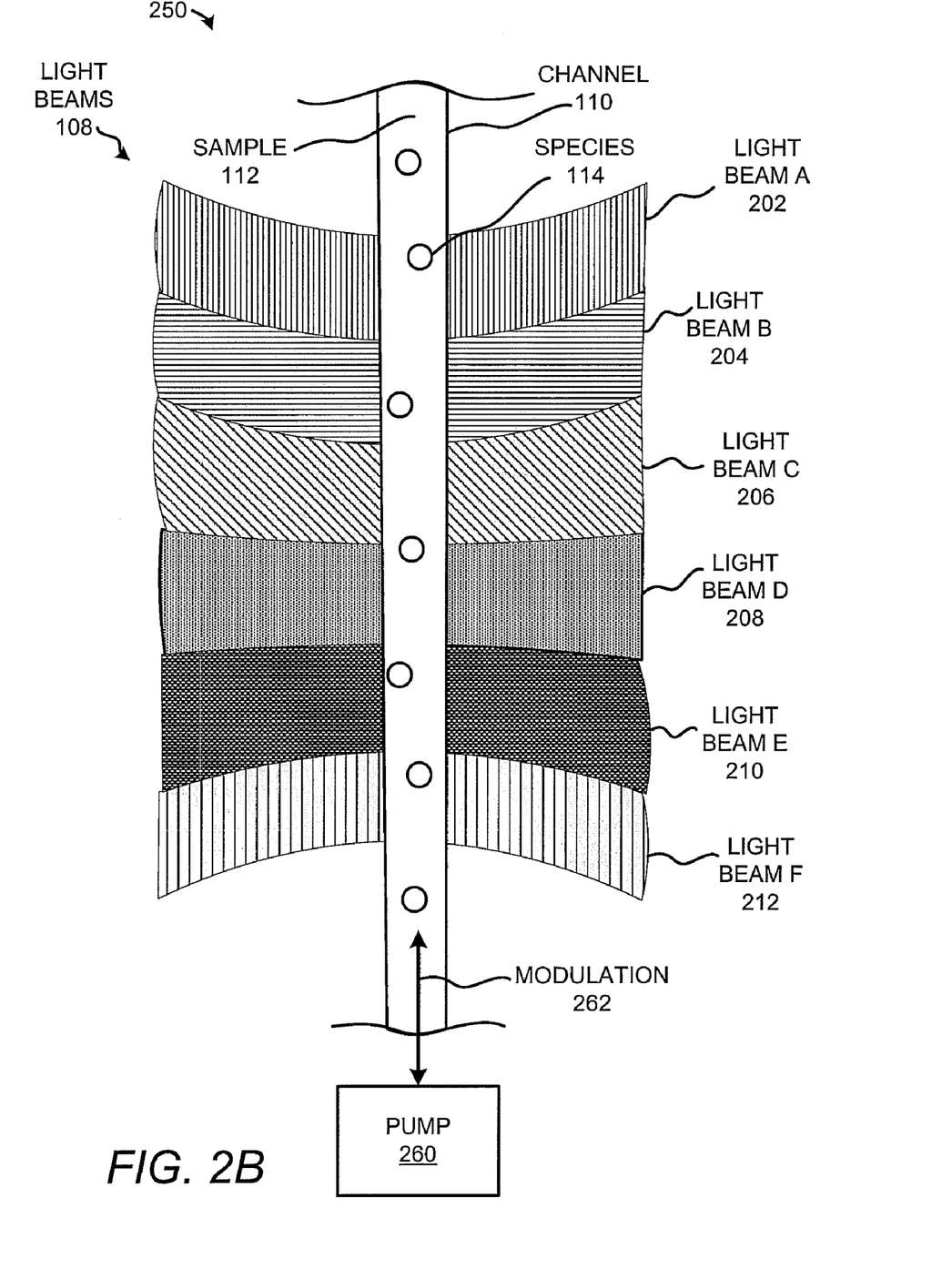

With reference now to FIG. 2A, there is shown a simplified and enlarged schematic diagram 200 of the channel 110, the sample 112, and the light beams 108 depicted in FIG. 1, according to an embodiment. The diagram 200 generally depicts the light beams 108 as being composed of a plurality of light beams 202-212 having different wavelengths and arranged as relatively distinct bands. By way of example, the light beam A 202 may comprise a wavelength of light that appears dark blue, the light beam B 204 may comprise a wavelength of light that appears blue, the light beam C 206 may comprise a wavelength of light that appears green, the light beam D 208 may comprise a wavelength of light that appears yellow, the light beam E 210 may comprise a wavelength of light that appears orange, and the light beam F 212 may comprise a wavelength of light that appears red. Although the light beams 202-212 have been depicted as being arranged in a particular order, the light beams 202-212 may be arranged in any order with respect to each other. In addition, the light beams 108 may include less than six different light beams 202-212. For instance, the light beams 108 may be composed of two or more of the light beams 202-212. Moreover, although the bands of light beams 202-212 have been depicted as being in close proximity to each other, gaps may exist between adjacent light beams 202-212 without departing from a scope of the invention.

In a first example, which corresponds to alternative A 140 in FIG. 1, the modulating element 130 is configured to modulate the light beams 202-212 with respect to the sample 112 as indicated by the arrow 220. In this example, the modulating element 130 is configured to cause the light beams 202-212 to oscillate across the sample 112 such that the sample 112 is irradiated by each of the light beams 202-212 during each modulation cycle. The modulating element 130 may cause the light beams 202-212 to oscillate across the sample 112 in any of a variety of different manners. For instance, the modulating element 130 may modulate the spatial positions of the one or more laser sources 102. As another example, the laser beam(s) 104 emitted by the laser source(s) 102 may be deflected by an electro-optic deflector (not shown) prior to irradiating the sample 112. In this example, the modulating element 130 is configured to modulate the electro-optic deflector to modulate the deflection of the laser beam(s) 104 and thereby cause the light beams 202-212 to oscillate across the sample 112.

In a second example, which corresponds to alternative B 142 in FIG. 1, the modulating element 130 is configured to modulate at least one of the spatial position and angle of the optical waveguide 106 to thereby modulate the illumination positions of the light beams 202-212 with respect to the sample 112. In a third example, which corresponds to alternative C in FIG. 1, the modulating element 130 is configured to modulate the spatial position of the channel 110 with respect to the light beams 202-212. In this example, the modulating element 130 is configured to cause the channel 110 to oscillate between the light beams 202-212 to thereby cause the sample 112 to be irradiated by each of the light beams 202-212 during each modulation cycle.

In the first, second, and third alternatives 140-144, the modulating element 130 may comprise any suitable mechanical device configured to modulate one or more of the laser source(s) 102, the optical waveguide 106 and the channel 110. Examples of suitable mechanical devices include MEMS devices, piezoelectric devices, a voice coil, etc.

In a fourth example, which corresponds to alternative D 146 in FIG. 1, the modulating element 130 is configured to modulate the position of the sample 112 with respect to the light beams 202-212. This example is depicted in FIG. 2B, which shows a simplified and enlarged schematic diagram 250 of the channel, 110, the sample 112, and the light beams 108 depicted in FIG. 1, according to another example. The diagram 250 in FIG. 2B is similar to the diagram 200 in FIG. 2A, except that the light beams 202-212 are rotated approximately 90 degrees. In addition, the modulating element 130 comprises a pump 260 configured to modulate the position of the sample 112 as indicated by the arrow 262. In this example, the pump 260 is configured to cause the at least a portion of the sample 112 to oscillate across the light beams 202-212 within the channel 110.

Figure 3:
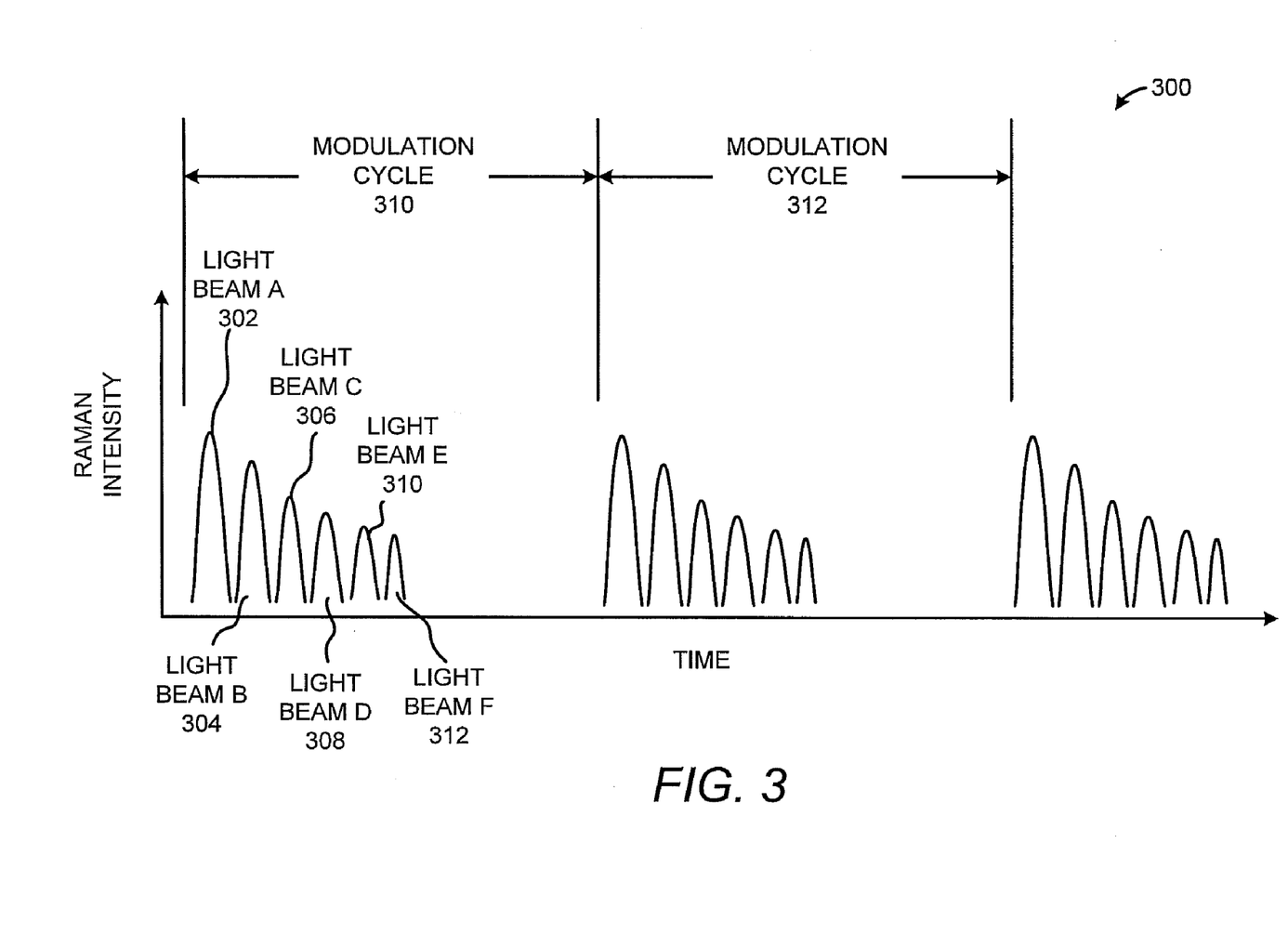
FIG. 3 illustrates a graph of the Raman light intensities emitted by a species that is irradiated by light beams of different wavelengths over a period of time, according to an embodiment of the invention.

In each of the examples discussed above, when the sample 112 is irradiated by the light beams 202-212, one or more of the species 114 contained in the sample 112 may substantially be held in place by an optical tweezing effect on the species 114 applied by the light beams 202-212. In this regard, the species 114 may substantially be held in place during multiple modulation cycles 312, 312 (FIG. 3). In addition, the species 114 are configured to emit Raman light and the intensities of the Raman light emissions from the species 114 may differ depending upon the wavelengths of the light beams 202-212. According to an embodiment, the detector(s) 120 are configured to detect the Raman light emissions and the post-signal processing unit 124 is configured to track the Raman light emissions as the relative spatial positions between the sample 112 and the light beams 202-212 oscillate. An example of the detected Raman light emission intensities at various times as the relative spatial positions are oscillated in modulation cycles is depicted in FIG. 3.

FIG. 3, more particularly, depicts a graph 300 of the Raman light intensities emitted by a species 114 that is irradiated by the light beams 202-206 over a period of time, according to an example. As shown therein, the Raman intensities 302-312 correspond to Raman emissions from a species 114 that is irradiated by the light beams 202-212 over multiple modulation cycles 310 and 312. As such, the ratio of the Raman light intensities for different excitation wavelengths 202-212 may be sampled. In this example, the modulation cycles 310 and 312 comprise a full cycle in which the sample 112 is sequentially irradiated by the light beams 202-212. The Raman emissions from the species 114 as the sample 112 is irradiated by the light beams 212 to 202 have not been depicted in FIG. 3, but those emissions may also be tracked without departing from a scope of the invention.

According to an embodiment, a species 114 may be determined to have been relatively accurately detected in the event that, for instance, the ratios of the Raman light intensities for the different excitation wavelengths 202-212 during multiple modulation cycles 310 and 312 are substantially equivalent to each other. Otherwise, in instances where the ratios of the Raman light intensities for the different excitation wavelengths 202-212 are not substantially equivalent to each other, a determination that a species has not been accurately detected may be made. The post-signal processing unit 124 may, for instance, include appropriate logic to analyze the Raman light intensity ratios to make the determinations discussed above.

According to another embodiment, the apparatus 100 is implemented to concurrently detect multiple species as the spatial relationship between the sample 112 and the light beams 202-212 is modulated. In this embodiment, the post-signal processing unit 124 or other processing device, such as a computer device, may parallel process the Raman light emissions received from multiple species 114.

With reference back to FIG. 1, and according to an embodiment, the one or more detectors 120 comprise at least one wide area detector configured to detect the Raman light emissions at multiple displacements. In addition or alternatively, and with particular reference to FIG. 4A, there is shown a simplified and enlarged diagram 400 of the detector(s) 120 formed of an array of detectors 402, according to an embodiment. The array of detectors 402 may be formed of a plurality of detectors, in which each of the detectors is configured to detect light received from a different location with respect to the channel 110. Also shown therein is a diffraction grating 404 which splits and diffracts the Raman light emissions 410 into several beams that travel into different directions and onto the deflectors of the detector array 402. Moreover, the detectors in the detector array 402 are configured to send electrical output signals 406 to the post-signal processing unit 124 as discussed above with respect to the detector(s) 120 in FIG. 1.

Figure 4A:
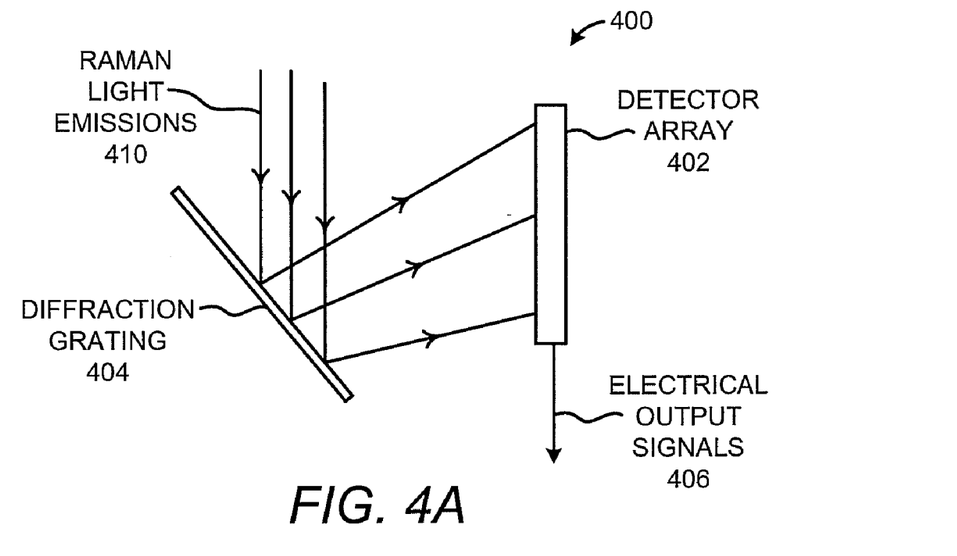
FIGS. 4A and 4B, respectively, illustrate simplified and enlarged diagrams of the detector(s) depicted in FIG. 1 formed of an array of detectors, according to embodiments of the invention.
Figure 4B:
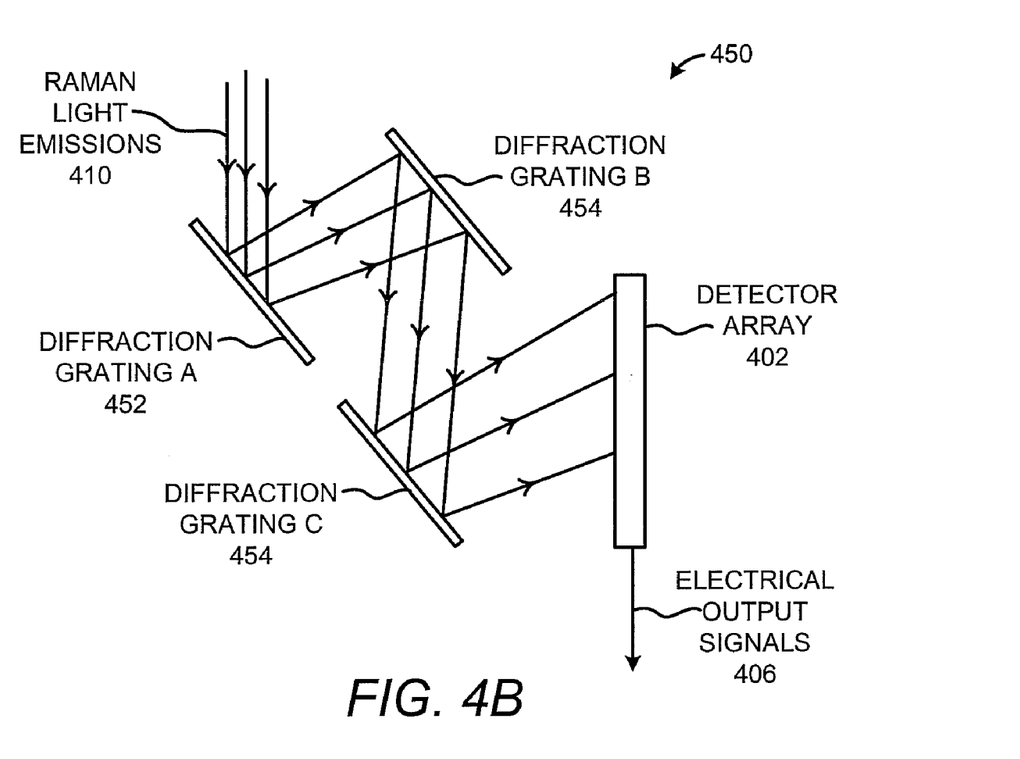

Turning now to FIG. 4B, there is shown a simplified and enlarged diagram 450 of the detector(s) 120 formed of an array of detectors 402, according to another embodiment. As shown therein, instead of being diffracted by a single diffraction grating 404 as in the diagram 400, in the diagram 450, the Raman light emissions 410 are diffracted by multiple diffraction gratings 452-456 prior to reaching the detector array 402. The multiple diffraction gratings 452-456 generally operate to increase the spacing between the Raman light emissions 410 to thus enable relatively larger detectors in the detector array 402 to be implemented in detecting the Raman light emissions 410 from multiple locations on the substrate 110. The detectors in the detector array 402 are also depicted as being configured to send electrical output signals 406 to the post-signal processing unit 124 as discussed above with respect to the detector(s) 120 in FIG. 1.

Figure 5:
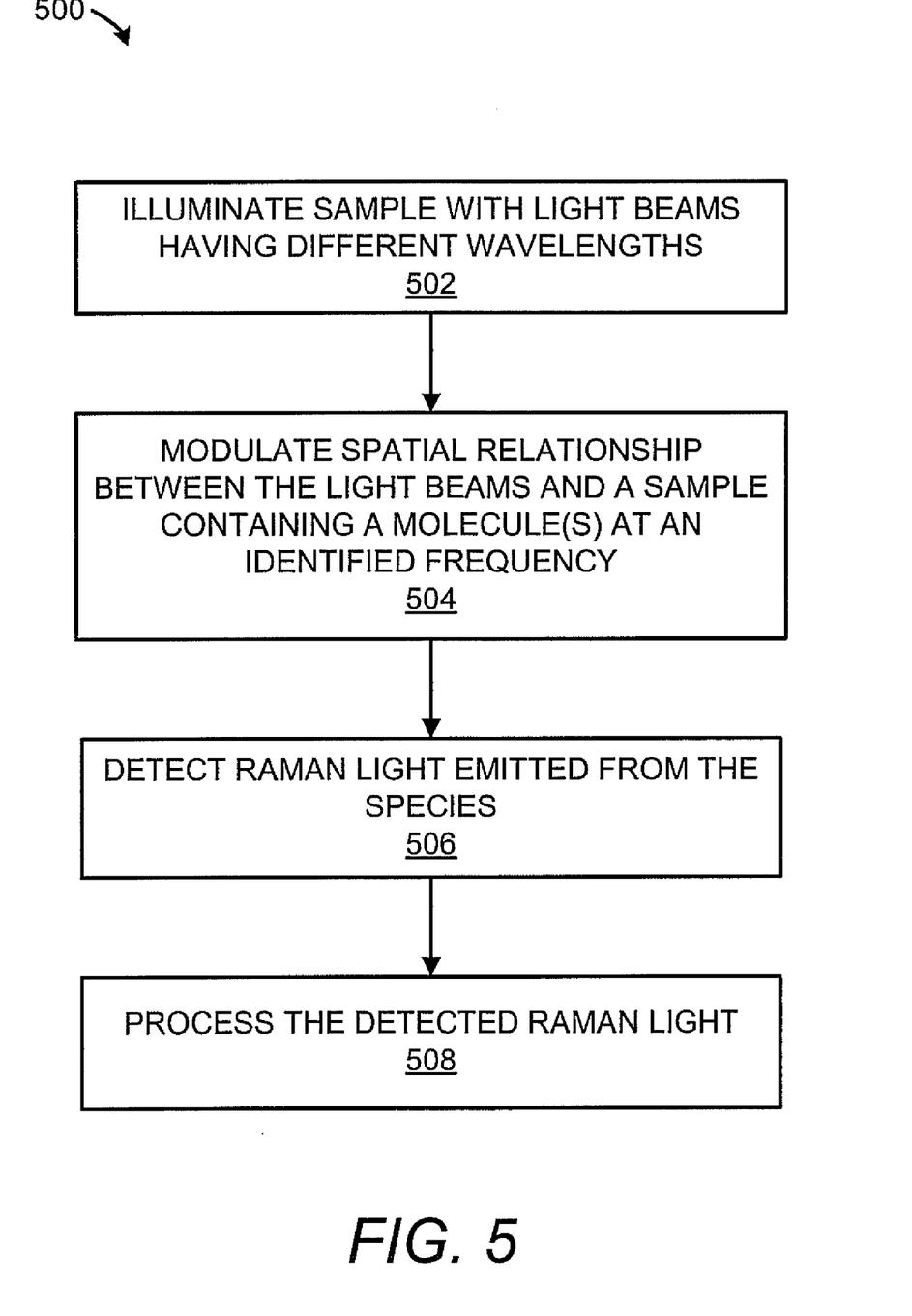
FIG. 5 depicts a flow diagram of a method for detecting at least one species through multi-wavelength Raman light detection, according to an embodiment of the invention.

Turning now to FIG. 5, there is shown a flow diagram of a method 500 for detecting at least one species 114 contained in a sample through multi-wavelength Raman light detection, according to an embodiment. It should be understood that the method 500 depicted in FIG. 5 may include additional steps and that some of the steps described herein may be removed and/or modified without departing from a scope of the method 500.

At step 502, the sample is illuminated with light beams 202-212 having different wavelengths, in which the light beams 202-212 are at least partially separated from each other as shown, for instance, in FIGS. 2A and 2B. The light beams 202-212 may illuminate the sample 112 in any of the manners discussed above with respect to the apparatus 100.

At step 504, a spatial relationship between the sample 112 and the light beams 202-212 is modulated to cause relative positions of the sample 112 and the light beams 202-212 to be oscillated, for instance, at an identified frequency of oscillation. The spatial relationship may be modulated in any of the manners discussed above with respect to the modulating element 130. In addition, as the spatial relationship is modulated, the sample 112 is configured to be illuminated with excitation light of different wavelengths 202-212. Moreover, Raman light is configured to be emitted or scattered from at least one species 114 contained in the sample 112 as the sample 112 receives the excitation light at the different wavelengths 202-212.

At step 506, the Raman light emitted 116 from the at least one species 114 is detected through operation of, for instance, the optical element(s) 118 and the detector(s) 120. As discussed above, the detector(s) 120 may comprise an array of detectors 402 configured to detect Raman light emitted 116 from species 114 located in multiple locations on the substrate 110.

At step 508, the detected Raman light emission(s) 116 are processed at the identified frequency to detect the species 114. More particularly, for instance, a lock-in detection technique may be implemented on the detected Raman light emission(s) 116 at the identified frequency of oscillation to thus enable the post-signal processing unit 124 to sample only the signal component ascribable to the species 114.

Some or all of the operations set forth in the method 500 may be contained as one or more utilities, programs, or subprograms, in any desired computer accessible or readable medium. In addition, the method 500 may be embodied by a computer program, which may exist in a variety of forms both active and inactive. For example, they may exist as software program(s) comprised of program instructions in source code, object code, executable code or other formats. Any of the above may be embodied on one or more computer readable storage devices or media.

Exemplary computer readable storage devices include conventional computer system RAM, ROM, EPROM, EEPROM, and magnetic or optical disks or tapes. Concrete examples of the foregoing include distribution of the programs on a CD ROM or via Internet download. It is therefore to be understood that any electronic device capable of executing the above-described functions may perform those functions enumerated above.

Figure 6:
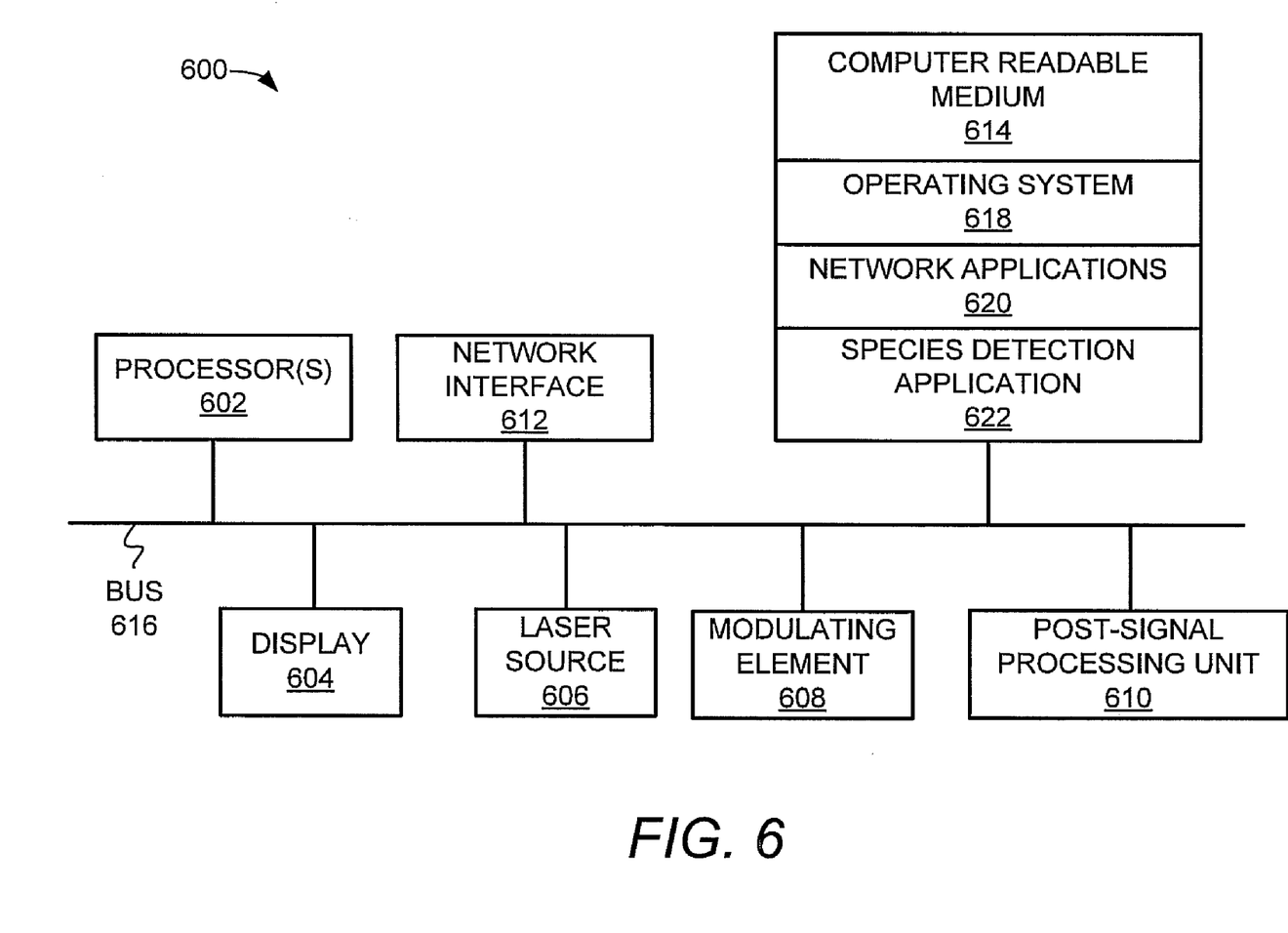
FIG. 6 shows a schematic representation of a computing device configured in accordance with embodiments of the present invention.

The method 500 may be implemented by a computing device, which may be a desktop computer, laptop, server, etc. Turning now to FIG. 6, there is shown a schematic representation of a computing device 600 configured in accordance with embodiments of the present invention. The computing device 600 includes one or more processors 602, such as a central processing unit; one or more display devices 604, such as a monitor; a laser source interface 606; a modulating element interface 608; a post-signal processing unit interface 610; one or more network interfaces 612, such as a Local Area Network LAN, a wireless 802.11x LAN, a 3G mobile WAN or a WiMax WAN; and one or more computer-readable mediums 614. Each of these components is operatively coupled to one or more buses 616. For example, the bus 616 may be an EISA, a PCI, a USB, a FireWire, a NuBus, or a PDS.

The computer readable medium 614 may be any suitable medium that participates in providing instructions to the processor 602 for execution. For example, the computer readable medium 610 can be non-volatile media, such as an optical or a magnetic disk; volatile media, such as memory; and transmission media, such as coaxial cables, copper wire, and fiber optics. Transmission media can also take the form of acoustic, light, or radio frequency waves.

The computer-readable medium 610 may also store an operating system 618, such as Mac OS, MS Windows, Unix, or Linux; network applications 620; and a species detection application 622. The operating system 618 may be multi-user, multiprocessing, multitasking, multithreading, real-time and the like. The operating system 618 may also perform basic tasks such as recognizing input from input devices, such as a keyboard or a keypad; sending output to the display 604, the laser source(s) 102, the modulating element 130, and the post-signal processing unit 124; keeping track of files and directories on medium 614; controlling peripheral devices, such as disk drives, printers, image capture device; and managing traffic on the one or more buses 616. The network applications 620 include various components for establishing and maintaining network connections, such as software for implementing communication protocols including TCP/IP, HTTP, Ethernet, USB, and FireWire.

The species detection application 622 provides various software components for detecting species 114 in samples 112, as described above. In certain embodiments, some or all of the processes performed by the species detection application 622 may be integrated into the operating system 618. In certain embodiments, the processes can be at least partially implemented in digital electronic circuitry, or in computer hardware, firmware, software, or in any combination thereof.

What has been described and illustrated herein is an embodiment along with some of its variations. The terms, descriptions and figures used herein are set forth by way of illustration only and are not meant as limitations. Those skilled in the art will recognize that many variations are possible within the spirit and scope of the subject matter, which is intended to be defined by the following claims—and their equivalents—in which all terms are meant in their broadest reasonable sense unless otherwise indicated.

What is claimed is:

1. An apparatus for detecting at least one species using multi-wavelength Raman light detection, said apparatus comprising:
   at least one laser source for illuminating a sample containing the at least one species with a plurality of light beams having different wavelengths, said plurality of light beams being at least partially distinct with respect to each other;
   a modulating element for modulating a spatial relationship between the sample and the plurality of light beams to cause relative positions of the sample and the plurality of light beams to be oscillated, wherein Raman light at differing intensity levels are configured to be emitted from the at least one species based upon the different wavelengths of the light beams illuminating the sample;
   at least one detector for detecting intensity levels of the Raman light emitted from the at least one species as the at least one species is illuminated by the light beams; and
   a post-signal processing unit configured to process the detected Raman light emission intensities to detect the at least one species.

2. The apparatus according to claim 1, wherein the post-signal processing unit further comprises a lock-in amplifier configured to process multiple Raman light signals collected from different excitation wavelengths of light with a common modulating frequency for the multiple Raman light signals.

3. The apparatus according to claim 1, wherein the post-signal processing unit is configured to identify patterns in the detected Raman light emission intensities upon being illuminated by the plurality of light beams over a period of time and to analyze the identified patterns to determine whether the at least one species has been detected.

4. The apparatus according to claim 1, wherein the modulating element is configured to modulate the sample to cause the position of the sample to oscillate across the plurality of light beams.

5. The apparatus according to claim 1, wherein the sample is configured to flow through a channel and wherein the modulating element is configured to modulate the sample to cause the sample to oscillate within the channel across the plurality of light beams.

6. The apparatus according to claim 1, wherein the modulating element is configured to modulate the illumination positions of the plurality of light beams with respect to the sample to cause the plurality of light beams to oscillate across the sample.

7. The apparatus according to claim 6, further comprising:
an optical waveguide through which at least one of the plurality of light beams travels; and
wherein the modulating element comprises a mechanical device configured to modulate at least one of a position and an angle of the optical waveguide with respect to the sample to cause the plurality of light beams to oscillate across the sample.

8. The apparatus according to claim 6, further comprising:
an electro-optic deflector configured to deflect at least one of the plurality of beams prior to illuminating the sample; and
wherein the modulating element is configured to modulate the electro-optic deflector to modulate the deflection of the plurality of light beams and cause the plurality of light beams to oscillate across the sample.

9. The apparatus according to claim 1, further comprising:
an optical element configured to split at least one laser beam emitted by the at least one laser source into the plurality of light beams having the different wavelengths.

10. The apparatus according to claim 1, further comprising:
a plurality of laser sources, each of the plurality of laser sources being configured to emit one of the plurality of light beams at different wavelengths.

11. A method for detecting at least one species contained in a sample through multi-wavelength Raman light emission detection, said method comprising:
illuminating the sample with a plurality of light beams having different wavelengths, said plurality of light beams being at least partially distinct from each other;
modulating a spatial relationship between the sample and the plurality of light beams to cause relative positions of the sample and the plurality of light beams to be oscillated, wherein Raman light at differing intensity levels are configured to be emitted from the at least one species based upon the different wavelengths of the light beams illuminating the sample;
detecting the Raman light emission intensity levels from the at least one species as the at least one species is illuminated by the light beams; and
processing the detected Raman light emission intensities to detect the at least one species.

12. The method according to claim 11, wherein processing the detected Raman light emissions further comprises operating a lock-in amplifier configured to process multiple Raman light signals collected from different excitation wavelengths of light with a common modulating frequency for the multiple Raman light signals.

13. The method according to claim 11, wherein processing the detected Raman light emissions further comprises:
identifying patterns in the detected Raman light emission intensities upon being illuminated by the plurality of light beams having the different wavelengths over a period of time; and
analyzing the identified patterns to determine whether the at least one species has been detected.

14. The method according to claim 11, wherein modulating the spatial relationship further comprises modulating the sample to cause the position of the sample to oscillate across the plurality of light beams.

15. The method according to claim 11, wherein the sample is configured to flow through a channel and wherein modulating the spatial relationship further comprises modulating the sample to cause the sample to oscillate within the channel across the plurality of light beams.

16. The method according to claim 11, wherein modulating the spatial relationship further comprises modulating the illumination positions of the plurality of light beams with respect to the sample to cause the plurality of light beams to oscillate across the sample.

17. The method according to claim 16, wherein the plurality of light beams are configured to travel through an optical waveguide and wherein modulating the spatial relationship further comprises modulating at least one of a position and an angle of the optical waveguide with respect to the sample to cause the plurality of light beams to oscillate across the sample.

18. The method according to claim 16, wherein the plurality of light beams are configured to be deflected by an electro-optic defector prior to illuminating the sample and wherein modulating the spatial relationship further comprises modulating the electro-optic deflector to modulate the deflection of the plurality of light beams and cause the plurality of light beams to oscillate across the sample.

19. A non-transitory computer readable storage medium on which is embedded one or more computer programs, said one or more computer programs implementing a method for detecting at least one species contained in a sample through multi-wavelength Raman light emission detection, said one or more computer programs comprising computer readable code for:
illuminating the sample with a plurality of light beams having different wavelengths, said plurality of light beams being at least partially distinct from each other;
modulating a spatial relationship between the sample and the plurality of light beams to cause relative positions of the sample and the plurality of light beams to be oscillated, wherein Raman light at differing intensity levels are configured to be emitted from the at least one species based upon the different wavelengths of the light beams illuminating the sample;
detecting the Raman light emission intensity levels from the at least one species as the at least one species is illuminated by the light beams; and
processing the detected Raman light emission intensities to detect the at least one species.

20. The non-transitory computer readable storage medium according to claim 19, said one or more computer programs further comprising a set of instructions for:
    wherein processing the detected Raman light emissions further comprises operating a lock-in amplifier configured to process multiple Raman light signals collected from different excitation wavelengths of light with a common modulating frequency for the multiple Raman light signals.

* * * * *

UNITED STATES PATENT AND TRADEMARK OFFICE
CERTIFICATE OF CORRECTION

PATENT NO. : 8,279,437 B2
APPLICATION NO. : 12/836097
DATED : October 2, 2012
INVENTOR(S) : Min Hu et al.

Page 1 of 1

It is certified that error appears in the above-identified patent and that said Letters Patent is hereby corrected as shown below:

On the Title Page, in Item (75), Inventors, line 3, delete "Huel" and insert -- Huei --, therefor.

In column 10, line 40, in Claim 18, delete "defector" and insert -- deflector --, therefor.

Signed and Sealed this
Ninth Day of April, 2013

Teresa Stanek Rea
*Acting Director of the United States Patent and Trademark Office*